US006815557B2

(12) United States Patent
Martin

(10) Patent No.: US 6,815,557 B2
(45) Date of Patent: Nov. 9, 2004

(54) TRYPTASE INHIBITORS

(75) Inventor: Thomas Martin, Constance (DE)

(73) Assignee: Altana Pharma AG, Constance (DE)

( * ) Notice: Subject to any disclaimer, the term of this patent is extended or adjusted under 35 U.S.C. 154(b) by 28 days.

(21) Appl. No.: 10/149,517

(22) PCT Filed: Dec. 16, 2000

(86) PCT No.: PCT/EP00/12840

§ 371 (c)(1),
(2), (4) Date: Sep. 9, 2002

(87) PCT Pub. No.: WO01/46128

PCT Pub. Date: Jun. 28, 2001

(65) Prior Publication Data

US 2003/0073720 A1 Apr. 17, 2003

(30) Foreign Application Priority Data

Dec. 20, 1999 (EP) ............................................ 99125382

(51) Int. Cl.$^7$ ....................... C07C 271/08; A61K 31/27
(52) U.S. Cl. .......................... 560/25; 560/26; 544/357; 514/483; 514/255
(58) Field of Search ..................... 560/25, 26; 544/357; 514/483, 255

(56) References Cited

U.S. PATENT DOCUMENTS 3,999,946 A * 12/1976 Patel et al. .................... 422/56
4,228,126 A * 10/1980 Patel et al. .................... 422/56

FOREIGN PATENT DOCUMENTS

| WO | 95 32945 | 12/1995 |
|----|----------|---------|
| WO | 96 09297 | 3/1996 |
| WO | 98 04537 | 2/1998 |
| WO | 99 12918 | 3/1999 |
| WO | 99 24395 | 5/1999 |
| WO | 99 24407 | 5/1999 |
| WO | 99 40073 | 8/1999 |
| WO | 99/40083 | 8/1999 |
| WO | 00/14097 | 3/2000 |
| WO | 01/10848 A2 | 2/2001 |
| WO | 01/19809 A1 | 3/2001 |

OTHER PUBLICATIONS

Caughey, G.H. et al., "Bis (5–Amidino–2–Benzimidazolyl) Methane and related Amidines are potent, reversible Inhibitors of mast Cell Tryptases", *The Journal of Pharmacology and Experimental Therapeutics*, vol. 264, No. 2, pp. 676–682, (1993).

Rice, Kenneth D. et al., "Inhibitors of Tryptase for the Treatment of Mast Cell–Mediated Diseases", *Current Pharmaceutical Design*, vol. 4, pp. 381–396, (1998).

Stürzebecher, Jorg et al., "Inhibition of Haman Mast Cell Tryptase by Benzamidine Derivatives", *Biol. Chem. Hoppe–Seyler*, vol. 373, pp. 1025–1030, (Oct. 1992).

Ono, Shin' ichio et al., "Syntheses and Evaluation of Amidinobenzofuran Derivatives as Tryptase Inhibitors", *Bioorganic & Medicinal Chemistry Letters*, No. 9, pp. 3285–3290, (1999).

Bertault, Marcel et al., "Synthesis and Solid–state Polymerization Properties of Symmetrical and Unsymmetrical Diacetylene Deivatives containing a 'Polymerogenic' Side Group", *J. Chem. Soc. Chem. Commun.*, pp. 163–166, (1988).

\* cited by examiner

*Primary Examiner*—Shailendra Kumar
(74) *Attorney, Agent, or Firm*—Nath & Associates PLLC; Todd L. Juneau; Sheldon M. McGee

(57) ABSTRACT

Compounds of formula (I), in which M, A1, A2, K1 and K2 have the meanings as indicated in the description are novel active tryptase inhibitors.

10 Claims, No Drawings

TRYPTASE INHIBITORS

This application is a 371 of PCT/EP00/12840, filed Dec. 16, 2000.

FIELD OF APPLICATION OF THE INVENTION

The invention relates to novel tryptase inhibitors which are used in the pharmaceutical industry for preparing medicaments.

KNOWN TECHNICAL BACKGROUND

The international applications WO95/32945, WO96/09297, WO98/04537, WO99/12918, WO99/24395, WO99/24407 and WO99/40073 describe low-molecular-weight bivalent compounds for use as tryptase inhibitors.

DESCRIPTION OF THE INVENTION

It has now been found that the compounds of the formula I, which are described in more detail below, have surprising and particularly advantageous properties.

The invention provides compounds of the formula I

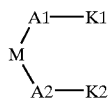
(I)

in which

M is a central building block of the formula below

n is 1 or 2,

U1 and U2 are identical or different and are methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—] or isopropylidene [—C(CH$_3$)$_2$—], A1 is —O—B1—A3—, —A5—B1—O—, —C(O)—, —C(O)—NH—, —NH—C(O)—, —O—C(O)—NH—, —NH—C(O)—O—, —NH—C(O)—NH— or —O—C(O)—O—, A2 is —O—B2—A4—, —A6—B2—O—, —C(O)—, —C(O)—NH—, —NH—C(O)—, —O—C(O)—NH—, —NH—C(O)—O—, —NH—C(O)—NH— or —O—C(O)—O—, A3 and A4 are identical or different and are —C(O)—, —C(O)—NH—, —NH—C(O)—, —O—C(O)—NH—, —NH—C(O)—O—, —NH—C(O)—NH— or —O—C(O)—O—, A5 and A6 are identical or different and are —C(O)—, —C(O)—NH—, —NH—C(O)—, —O—C(O)—NH—, —NH—C(O)—O—, —NH—C(O)—NH— or —O—C(O)—O—, B1 and B2 are identical or different and are 1-4C-alkylene, K1 is —B3—X1, —B3—Y1 or —B3—Z1—B5—X1, K2 is —B4—X2, —B4—Y2 or —B4—Z2—B6—X2, B3 and B4 are identical or different and are a bond or 1-4C-alkylene, B5 and B6 are identical or different and are a bond or 1-2C-alkylene, X1 and X2 are identical or different and are amino, aminocarbonyl or amidino, Y1 and Y2 are imidazol-1-yl, Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 35, preferably 24 to 29, bonds have to be present, the salts of these compounds, and the N-oxides of the nitrogen-containing heteroaryls, heteroarylenes and heterocycloalkylenes, and their salts, where all those compounds are excluded in which one or more of the variables B3, B4, B5 or B6 adopts the meaning of a bond and there would consequently be a direct linkage of two heteroatoms.

1-4C-alkylene represents straight-chain or branched 1-4C-alkylene radicals, for example the methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—], 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—] or the 1-methylethylene [—CH(CH$_3$)—CH$_2$—] radicals.

By definition, the groups Z1 and Z2 are located between groups B3 and B5 (—B3—Z1—B5—) and B4 and B6 (—B4—Z2—B6—), respectively. Accordingly, in the divalent groupings mentioned by way of example (for example 3,6-indolylene), the first number indicates the point of attachment to the group B3 and B4, respectively, and the second number indicates the point of attachment to the group B5 and B6, respectively.

In the context of this application, the term "terminal nitrogen atom" means in each case a nitrogen atom in the groups designated X1, X2, Y1 and Y2.

If the group X1 or X2 contains only one nitrogen atom, this nitrogen atom is the terminal nitrogen atom.

If the group X1 or X2 contains a plurality of nitrogen atoms, the nitrogen atom which is furthest from the atom by means of which the bond to the group B3 (B5) or B4 (B6) is established is the terminal nitrogen atom.

If the group Y1 or Y2 contains only one ring nitrogen atom, this ring nitrogen atom is the terminal nitrogen atom.

If the group Y1 or Y2 contains a plurality of ring nitrogen atoms, the ring nitrogen atom which is furthest from the atom by means of which the bond to the group B3 or B4 is established is the terminal nitrogen atom.

According to the invention, the direct route between the nitrogen atoms which act as terminal nitrogen atoms in the groups defined as X1 (Y1) or X2 (Y2) is considered to be the number of bonds which is obtained by counting the bonds which represent the shortest possible connection between the terminal nitrogen atoms.

The following example is meant to illustrate the determination of the number of bonds on the direct route between two terminal nitrogen atoms:

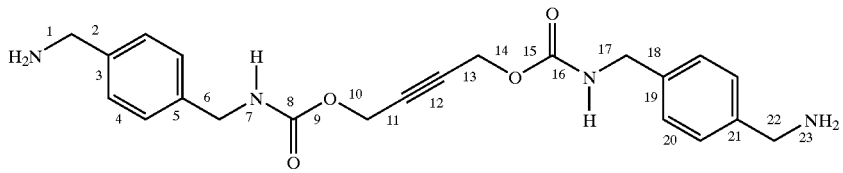

Here, the direct route comprises 23 bonds.

Preference is given to those compounds of the formula I whose molecular weight is below 600 g/mol.

Particular preference is given to those compounds of the formula I whose molecular weight is below 500 g/mol.

Suitable salts for compounds of the formula I are all acid addition salts. Particular mention may be made of the pharmaceutically acceptable salts of inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the salts are employed in salt preparation—depending on whether a mono- or poly-basic acid is concerned and depending on which salt is desired—in an equimolar quantitative ratio or one differing therefrom.

Pharmacologically unacceptable salts which can be obtained initially as process products, for example in the preparation of the compounds according to the invention on an industrial scale, are converted into pharmacologically acceptable salts by processes known to the person skilled in the art.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Compounds of the formula I which are to be emphasized are those in which

M is a central building block of the formula below

n is 1 or 2,

U1 and U2 are identical or different and are methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—] or isopropylidene [—C(CH$_3$)$_2$—], A1 is —O—B1—A3—, —A5—B1—O—, —NH—C(O)—, —O—C(O)—NH—, —NH—C(O)—O—, —NH—C(O)—NH— or —O—C(O)—O—, A2 is —O—B2—A4—, —A6—B2—O—, —NH—C(O)—, —O—C(O)—NH—, —NH—C(O)—O—, —NH—C(O)—NH— or —O—C(O)—O—, A3 and A4 are identical or different and are —C(O)—NH—, —NH—C(O)—, —O—C(O)—NH—, —NH—C(O)—O—, —NH—C(O)—NH— or —O—C(O)—O—, A5 and A6 are identical or different and are —NH—C(O)—, —O—C(O)—NH—, —NH—C(O)—O—, —NH—C(O)—NH— or —O—C(O)—O—, B1 and B2 are identical or different and are 1-2C-alkylene, K1 is —B3—Z1—B5—X1, K2 is —B4—Z2—B6—X2, B3 and B4 are identical or different and are a bond or 1-2C-alkylene, B5 and B6 are identical or different and are a bond or 1-2C-alkylene, X1 and X2 are identical or different and are amino or amidino, Z1 and Z2 are identical or different and are 1,3-phenylene, 1,4-phenylene, 1,3-cyclohexylene or 1,4-cyclohexylene, and where on the direct route between the terminal nitrogen atoms 20 to 35, preferably 24 to 29, bonds have to be present, and the salts of these compounds.

Compounds of the formula I which are to be particularly emphasized are those in which M is a central building block of the formula below

n is 1 or 2,

U1 and U2 are identical or different and are methylene [—CH$_2$—] or isopropylidene [—C(CH$_3$)$_2$—], A1 is —O—B1—A3— or —O—C(O)—NH—, A2 is —O—B2—A4— or —O—C(O)—NH—, where A3 is —O—C(O)—NH— and A4 is —O—C(O)—NH—, B1 and B2 are identical and are ethylene, K1 is —B3—Z1—B5—X1, K2 is —B4—Z2—B6—X2, B3 and B4 are identical and are methylene, B5 and B6 are identical and are methylene, X1 and X2 are identical and are amino, Z1 and Z2 are identical or different and are 1,3-phenylene, 1,4-phenylene or 1,4-cyclohexylene, and the salts of these compounds.

Preferred compounds of the formula I are those in which

M is a central building block of the formula below

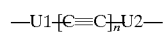

n is 1 or 2,

U1 and U2 are identical and are methylene [—CH$_2$—],

A1 is —O—B1—A3— or —O—C(O)—NH—,

A2 is —O—B2—A4— or —O—C(O)—NH—, where

A3 is —O—C(O)—NH— and

A4 is —O—C(O)—NH—,

B1 and B2 are identical and are ethylene,

K1 is —B3—Z1—B5—X1,

K2 is —B4—Z2—B6—X2,

B3 and B4 are identical and are methylene,

B5 and B6 are identical and are methylene,

X1 and X2 are identical and are amino,

Z1 and Z2 are identical or different and are 1,3-phenylene or 1,4-phenylene, and the salts of these compounds.

Especially preferred compounds of the formula I are 1,4-bis-(3-aminomethylbenzylaminocarbonyl-1,2-dioxyethyl)-2-butyne, 1,6-bis-(4-aminomethylbenzylaminocarbonyl-1-oxy)-2,4-hexadiyne and 1,4-bis-(3-aminomethylbenzylaminocarbonyl-1-oxy)-2-butyne, and the salts of these compounds.

The compounds of the formula I are constructed from a large number of building blocks (M, A1, A2, A3, A4, A5, A6, B1, B2, B3, B4, B5, B6, X1, X2, Y1, Y2, Z1 and Z2). In principle, they can be synthesized starting with any of these building blocks. If the compounds of the formula I are constructed largely symmetrically, it is favorable to start the synthesis with the central building block M, whereas in the case of predominantly asymmetrical compounds of the formula I a synthesis starting with one of the end groups K1 or K2 may be advantageous.

Suitable starting materials for synthesizing the compounds of the formula I according to the invention are, for example, 2-butyne-1,4-diol, 2,4-hexadiyne-1,6-diol, 2,4-dimethyl-3-hexyne-2,5-diol or 2,7-dimethyl-3,5-octadiyne-2,7-diol.

Here, the building blocks are linked using always the same pattern, known per se to the person skilled in the art.

It is known to the person skilled in the art that the compounds of the formula I can either be synthesized building block by building block, or by initially constructing relatively large fragments consisting of several individual building blocks, which can then be joined to give the complete molecule.

Owing to the meanings which the individual building blocks of the compounds of the formula I can assume, ether [—O—], keto [—C(O)—], amide [—C(O)—NH—, —NH—C(O)—], carbamate [—NH—C(O)—O—, —O—C(O)—NH—], carbamide [—NH—C(O)—NH—] or carbonate [—O—C(O)—O—] bridges are present in the compounds of the formula I.

How to prepare such bridges is known per se to the person skilled in the art; suitable methods and starting materials for their preparation are described, for example, in March, Advanced Organic Chemistry, Reactions, Mechanisms and Structure, Third Edition, 1985, John Wiley & Sons.

Ether bridges can be prepared, for example, by the method of Williamson.

Keto bridges can be introduced, for example, as a component of relatively large building blocks, such as, for example, carboxylic acid derivatives.

There is also a large number of known methods for preparing amide bridges. An example which may be mentioned here is the reaction of acyl chlorides with primary or secondary amines. Furthermore, reference is also made to all the methods which have been developed for peptide chemistry.

Carbamate bridges can be prepared, for example, by reacting chloroformates with amines. The chloroformates for their part can be synthesized from alcohols and phosgene. A further variant for constructing carbamate bridges is the addition of alcohols to isocyanates. Similarly to carbamate bridges, it is possible to prepare carbonate bridges starting from chloroformates, by reaction with alcohols (instead of amines).

Carbamide bridges can be prepared, for example, by reacting isocyanates with amines.

The preparation of compounds of the formula I may be shown in an exemplary manner using the reaction schemes below. Reaction scheme 1 shows the preparation of the exemplary compound 1. Reaction scheme 2 shows the preparation of the exemplary compound 2. Reaction scheme 3 shows the preparation of the exemplary compound 3. Other compounds of the formula I can be prepared analogously, or by using the abovementioned methods known per se to the person skilled in the art.

Reaction scheme 1:

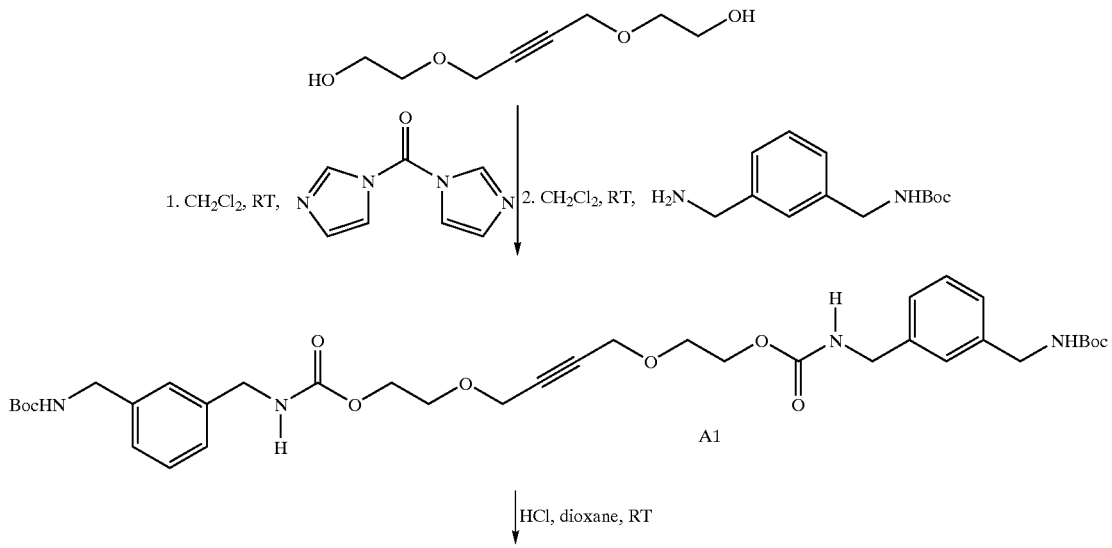

7 8
-continued
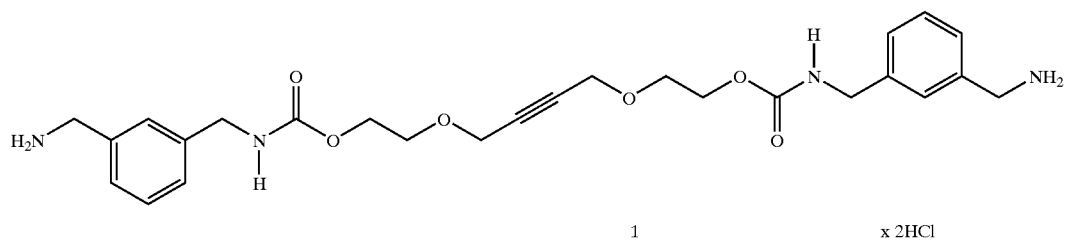
1 x 2HCl
Reaction scheme 2:
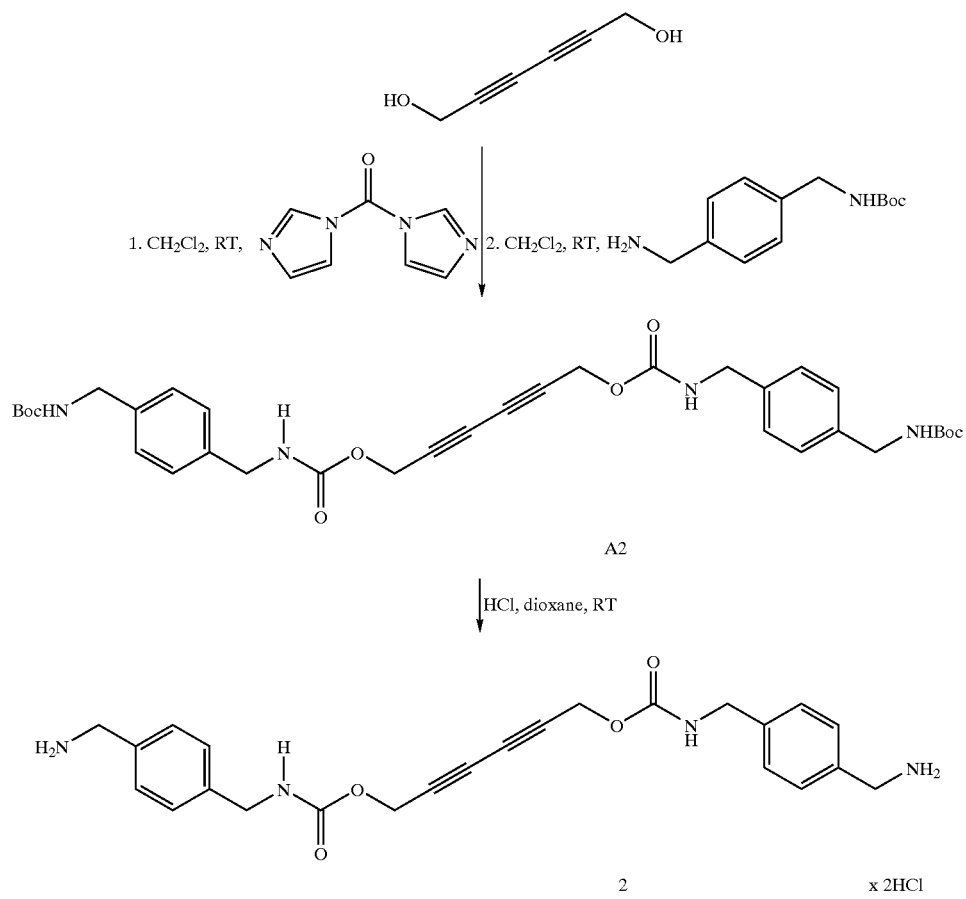
2 x 2HCl
Reaction scheme 3:
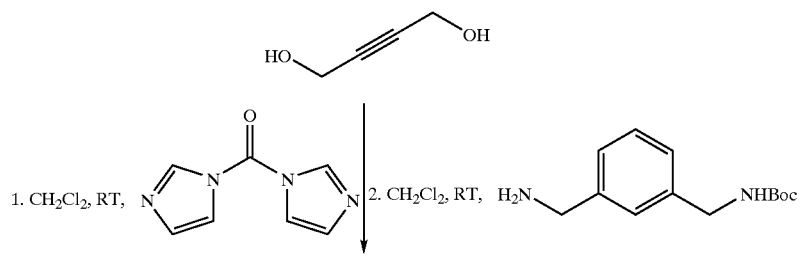

-continued

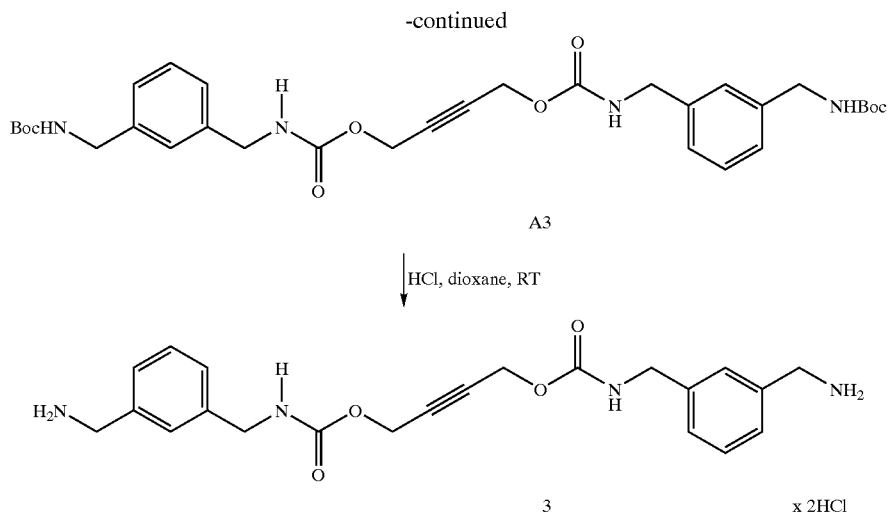

A3

↓ HCl, dioxane, RT 3    x 2HCl

It is also possible to convert compounds of the formula I by derivatization into other compounds of the formula I. Thus, for example, compounds of the formula I having a nitrogen-containing heteroaryl, heteroarylene or heterocycloalkylene building block can be converted by oxidation into the corresponding N-oxides.

The N-oxidation is carried out in a manner which is likewise known to the person skilled in the art, for example using hydrogen peroxide in methanol or m-chloroperoxybenzoic acid in dichloromethane at room temperature. Which reaction conditions are required in the particular case for carrying out the process is known to the person skilled in the art owing to his expert knowledge.

It is furthermore known to the person skilled in the art that if there are a number of reactive centers on a starting material or intermediate, it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent under reduced pressure and recrystallizing the resulting residue from a suitable solvent or subjecting it to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

The examples below serve to illustrate the invention in more detail without restricting it. Likewise, further compounds of the formula I, whose preparation is not explicitly described, can be prepared in an analogous manner or in a manner familiar per se to the person skilled in the art using customary process techniques.

In the examples below, the abbreviation RT stands for room temperature, calc. for calculated and MS for mass spectrometry. The compounds mentioned by way of example and their salts are the preferred subject of the invention.

EXAMPLES

End Products:

General Procedure

A solution of the Boc-protected divalent compound (A1—A3; 1.0 mmol) in question in dioxane (4 ml) is admixed with a saturated solution of HCl in dioxane (4 ml, 18.0 mmol) and stirred at RT for 4 h. The resulting precipitate is filtered off under an $N_2$ atmosphere and washed first with dioxane (2×5 ml) and then with diethyl ether (3×5 ml). Drying under reduced pressure gives the title compounds (end products 1–3) as colorless solids.

1. 1,4-Bis-(3-aminomethylbenzylaminocarbonyl-1, 2-dioxyethyl)-2-butyne dihydrochloride MS: calc.: $C_{26}H_{34}N_4O_6$ (498.8), found: [MH$^+$] 499.1

2. 1,6-Bis-(4-aminomethylbenzylaminocarbonyl-1-oxy-2,4-hexadiyne dihydrochloride MS: calc.: $C_{24}H_{26}N_4O_4$ (434.5), found: [MH$^+$] 435.4

3. 1,4-Bis-(3-aminomethylbenzylaminocarbonyl-1-oxy)-2-butyne dihydrochloride

MS: calc.: $C_{22}H_{26}N_4O_4$ (410.7), found: [MH$^+$] 411.1

Starting Materials:

General Procedure

N,N-carbonyldiimidazole (486 mg, 3.0 mmol) is added to a solution of the respective bis-diol-alkyne 1.0 mmol) in absolute $CH_2Cl_2$ (5 ml), and the mixture is stirred at RT for 0.5 h. The reaction solution is diluted with $CH_2Cl_2$ (5 ml) and extracted with a semisaturated aqueous NaCl solution (10 ml). The organic phase is dried over $MgSO_4$, filtered off and concentrated under reduced pressure. The resulting residue is taken up in absolute $CH_2Cl_2$ (5 ml), the Boc-protected amino compound in question (2.2 mmol, 1-aminomethyl-3-N-tert-butoxycarbonylaminomethylbenzene or 1-aminomethyl-4-N-tert-butoxycarbonylaminomethylbenzene) is added and the mixture is stirred at RT overnight. The reaction solution is diluted with $CH_2Cl_2$ (5 ml) and extracted with a semisaturated aqueous NaCl solution (10 ml). The organic phase is dried over $MgSO_4$, filtered off and concentrated under reduced pressure. Further purification is carried out by recrystallization using methanol/diethyl ether. The title compounds (A1—A3) are obtained as colorless solids.

A1. 1,4-Bis-(3-N-tert-butoxycarbonylaminomethylbenzylaminocarbonyl-1,2-dioxyethyl)-2-butyne MS: calc.: $C_{36}H_{50}N_4O_{10}$ (698.8), found: [MH$^+$] 691.1; [MNa$^+$] 721.1

A2. 1,6-Bis-(4-N-tert-butoxycarbonylaminomethylbenzylaminocarbonyl-1-oxy)-2,4-hexadiyne MS: calc.: $C_{34}H_{42}N_4O_8$ (634.7), found: [MH$^+$] 635.4; [MNa$^+$] 657.4

A3. 1,4-Bis-(3-N-tert-butoxycarbonylaminomethylbenzylaminocarbonyl-1-oxy)-2-butyne MS: calc.: $C_{32}H_{42}N_4O_8$ (610.7), found: [MH$^+$] 611.0; [MNa$^+$] 633.0

Commercial Utility

As tryptase inhibitors, the compounds according to the invention have useful pharmacological properties which make them commercially utilizable. Human tryptase is a serin protease which is the main protein in human mast cells. Tryptase comprises eight closely related enzymes (α1, α2, β1a, β1b, β2, β3, mMCP-7-like-1, mMCP-7-like-2; 85 to 99% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815; Pallaoro et al., J. Biol. Chem. 274 (1999) 3355–3362). However, only the β-tryptases (Schwartz et al., J. Clin. Invest. 96 (1995) 2702–2710; Sakai et al., J. Clin. Invest. 97 (1996) 988–995) are activated intracellularly and stored in catalytically active form in secretory granules. Compared with other known serin proteases, such as, for example, trypsin or chymotrypsin, tryptase has some special properties (Schwartz et al., Methods Enzymol. 244, (1994), 88–100, G. H. Caughey, "Mast cell proteases in immunology and biology". Marcel Dekker, Inc., New York, 1995). Tryptase from human tissue has a noncovalently-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly since an increased tryptase concentration was observed in a number of disorders of this type. Thus, tryptase is associated, inter alia, with the following diseases: acute and chronic (in particular inflammatory and allergen-induced) airway disorders of various origins (for example bronchitis, allergic bronchitis, bronchial asthma, COPD); interstitial lung disorders; disorders based on allergic reactions of the upper airways, (pharynx, nose) and the adjacent regions (for example paranasal sinuses, conjunctivae), such as, for example allergic conjunctivitis and allergic rhinitis; disorders of the arthritis type (for example rheumatoid arthritis); autoimmune disorders, such as multiple sclerosis; furthermore periodontitis, anaphylaxis, interstitial cystitis, dermatitis, psoriasis, sclerodermia/systemic sclerosis, inflammatory intestinal disorders (Crohn's disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, Chapter 3.3.1–3.3.23).

The inhibitions according to the invention are characterized by low toxicity, good enteral absorption (high bioavailability), a large therapeutic breadth and the absence of significant side effects.

A further subject of the invention relates to the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by processes which are known per se and familiar to the person skilled in the art. As medicaments, the compounds according to the invention (=active compounds) are either employed as such, or preferably in combination with suitable pharmaceutical excipients, for example in the form of tablets, coated tablets, capsules, suppositories, patches, emulsions, suspension, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, they are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram per day.

Biological Investigations

The documented pathophysiological effects of mast cell tryptase are caused directly by the enzymatic activity of the protease. Accordingly, they are reduced or blocked by inhibitors which inhibit the enzymatic activity of the tryptase. A suitable measure for the affinity of a reversible inhibitor to the target protease is the equilibrium dissociation constant $K_i$ of the enzyme-inhibitor complex. This $K_i$ value can be determined via the effect of the inhibitor on the tryptase-induced cleavage of a chromogenic peptide-p-nitroanilide substrate or a fluorogenic peptide-aminomethylcoumarin substrate.

Methodology

The dissociation constants for the tryptase-inhibitor complexes are determined under equilibrium conditions in accordance with the general proposals of Bieth (Bieth J G, Pathophysiological Interpretation of kinetic constants of protease inhibitors, Bull. Europ. Physiopath. Resp. 16:183–195, 1980) and the methods of Sommerhoff et al. (Sommerhoff C P et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is isolated from lung tissue or prepared recombinantly; the specific activity of the protease, determined by titration, is usually greater than 85% of the theoretical value. In the presence of heparin (0.1–50 µg/ml) for stabilizing the protease, constant amounts of the tryptase are incubated with increasing amounts of the inhibitors. After an equilibrium between the reaction partners has formed, the remaining enzyme activity after addition of the peptide-p-nitroanilide substrate tos-Gly-Pro-arg-pNA is determined and the cleavage of the latter is monitored at 405 nm for 3 min. Alternatively, the remaining enzymatic activity can also be determined using fluorogenic substrates. The apparent dissociation constants $K_{iapp}$ (i.e. in the presence of substrate) are subsequently determined by adapting the enzyme rates to the general equation for reversible inhibitors (Morrison J F, Kinetics of the reversible inhibition of enzyme-catalyzed reactions by tight-binding inhibitors, Biochim. Biophys. Acta 185, 269–286, 1969) using non-linear regression:

$$V_1/V_0 = 1 - \{E_t + I_t + K_{iapp} - [(E_t + I_t + K_{iapp})^2 - 4E_t I_t]^{1/2}\}/2E_t$$

$V_1$ and $V_0$ are the rates in the presence and absence, respectively, of the inhibitor, and $E_t$ and $I_t$ are the tryptase and inhibitor concentrations, respectively.

The apparent dissociation constants determined for the compounds according to the invention are shown in Table A below, where the numbers of the compounds correspond to the numbers of the compounds in the examples.

TABLE A

Inhibition of human tryptase

| Compound | $K_{iapp}$ (µM) |
|---|---|
| 1 | 0.006 |
| 2 | 0.45 |
| 3 | 0.1 |

What is claimed is:
1. A compound of the formula I

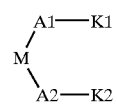
(I)

in which
M is a central building block of the formula below

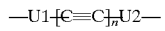

n is 1 or 2,
U1 and U2 are identical or different and are methylene [—CH₂—], ethylene [—CH₂—CH₂—], trimethylene [—CH₂—CH₂—CH₂—], tetramethylene [—CH₂—CH₂—CH₂—CH₂—], or isopropylidene [—C(CH₃)₂—],
A1 is —O—B1—A3—, —A5—B1—O—, —C(O)—, —C(O)—NH—, —NH—C(O)—, —O—C(O)—NH—, —NH—C(O)—O—, —NH—C(O)—NH— or —O—C(O)—O—,
A2 is —O—B2—A4—, —A6—B2—O—, —C(O)—, —C(O)—NH—, —NH—C(O)—, —O—C(O)—NH—, —NH—C(O)—O—, —NH—C(O)—NH— or —O—C(O)—O—,
A3 and A4 are identical or different and are —C(O)—, —C(O)—NH—, —NH—C(O)—, —O—C(O)—NH—, —NH—C(O)—O—, —NH—C(O)—NH— or —O—C(O)—O—,
A5 and A6 are identical or different and are —C(O)—, —C(O)—NH—, —NH—C(O)—, —O—C(O)—NH—, —NH—C(O)—O—, —NH—C(O)—NH— or —O—C(O)—O—,
B1 and B2 are identical or different and are 1-4C-alkylene,
K1 is —B3—X1, —B3—Y1 or —B3—Z1—B5—X1,
K2 is —B4—X2, —B4—Y2 or —B4—Z2—B6—X2,
B3 and B4 are identical or different and are a bond or 1-4C-alkylene,
B5 and B6 are identical or different and are a bond or 1-2C-alkylene,
X1 and X2 are identical or different and are amino, aminocarbonyl or amidino,
Y1 and Y2 are imidazol-1-yl,
Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene,
and where on the direct route between the terminal nitrogen atoms 20 to 35 bonds have to be present, or a hydrate, solvate, salt, hydrate of a salt or solvate of a salt thereof, an N-oxide of the nitrogen-containing heteroaryls, heteroarylenes and heterocycloalkylenes or a hydrate, solvate, salt, hydrate of a salt or solvate of a salt thereof, where all those compounds are excluded in which one or more of the variables B3, B4, B5 or B6 adopts the meaning of a bond and there would consequently be a direct linkage of two heteroatoms.

2. A compound of the formula I according to claim 1, in which

M is a central building block of the formula below

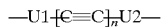

n is 1 or 2,

U1 and U2 are identical or different and are methylene [—$CH_2$—], ethylene [—$CH_2$—$CH_2$—], trimethylene [—$CH_2$—$CH_2$—$CH_2$—], tetramethylene [—$CH_2$—$CH_2$—$CH_2$—$CH_2$—], or isopropylidene [—$C(CH_3)_2$—], A1 is —O—B1—A3—, —A5—B1—O—, —C(O)—, —C(O)—NH—, —NH—C(O)—, —O—C(O)—NH—, —NH—C(O)—O—, —NH—C(O)—NH—or —O—C(O)—O—, A2 is —O—B2—A4—, —A6—B2—O—, —NH—C(O)—, —O—C(O)—NH—, —NH—C(O)—O—, —NH—C(O)—NH—, or —O—C(O)—O—, A3 and A4 are identical or different and are —C(O)—NH—, —NH—C(O)—, —O—C(O)—NH—, —NH—C(O)—O—, —NH—C(O)—NH—, or —O—C(O)—O—, A5 and A6 are identical or different and are —NH—C(O)—, —O—C(O)—NH—, —NH—C(O)—O—, —NH—C(O)—NH—or —O—C(O)—O—, B1 and B2 are identical or different and are 1-2C-alkylene, K1 is —B3—Z1—B5—X1, K2 is —B4—Z2—B6—X2, B3 and B4 are identical or different and are a bond or 1-2C-alkylene, B5 and B6 are identical or different and are a bond or 1-2C-alkylene, X1 and X2 are identical or different and are amino or amidino, Z1 and Z2 are identical or different and are 1,3-phenylene, 1,4-phenylene, 1,3-cyclohexylene or 1,4-cyclohexylene, and where on the direct route between the terminal nitrogen atoms 20 to 35 bonds have to be present, or a hydrate, solvate, salt, hydrate of a salt or solvate of a salt thereof.

3. A compound of the formula I according to claim 1 in which

M is a central building block of the formula below

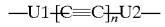

n is 1 or 2,

U1 and U2 are identical or different and are methylene [—$CH_2$—]or isopropylidene [—$C(CH_3)_2$—], A1 is —O—B1—A3—or —O—C(O)—NH—, A2 is —O—B2—A4—or —O—C(O)—NH—, where
A3 is —O—C(O)—NH—, and
A4 is —O—C(O)—NH—, B1 and B2 are identical and are ethylene, K1 is —B3—Z1—B5—X1, K2 is —B4—Z2—B6—X2, B3 and B4 are identical and are methylene, B5 and B6 are identical and are methylene, X1 and X2 are identical and are amino, Z1 and Z2 are identical or different and are 1,3-phenylene, 1,4-phenylene or 1,4-cyclohexylene, or a hydrate, solvate, salt, hydrate of a salt or solvate of a salt thereof.

4. A compound of the formula I according to claim 1 in which

M is a central building block of the formula below

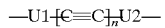

n is 1 or 2,

U1 and U2 are identical or different and are methylene [—$CH_2$—],

A1 is —O—B1—A3—or —O—C(O)—NH—,

A2 is —O—B2—A4—or —O—C(O)—NH—, where
A3 is —O—C(O)—NH—, and
A4 is —O—C(O)—NH—,

B1 and B2 are identical and are ethylene,

K1 is —B3—Z1—B5—X1,

K2 is —B4—Z2—B6—X2,

B3 and B4 are identical and are methylene,

B5 and B6 are identical and are methylene,

X1 and X2 are identical and are amino,

Z1 and Z2 are identical or different and are 1,3-phenylene, 1,4-phenylene or a hydrate, solvate, salt, hydrate of a salt or solvate of a salt thereof.

5. A compound of the formula I according to claim 1 with the chemical designation 1,4-bis-(3-aminomethylbenzylaminocarbonyl-1,2-dioxyethyl)—2-butyne, 1,6-bis-(4-aminomethylbenzylaminocarbonyl-1-oxy)-2,4-hexadiyne and 1,4-bis-(3-aminomethylbenzylaminocarbonyl-1-oxy)-2-butyne, or a hydrate, solvate, salt, hydrate of a salt or solvate of a salt thereof.

6. A compound of the formula I according to claim 1, in which on the direct route between the terminal nitrogen atoms 24 to 29 bonds have to be present.

7. A compound of the formula I according to claim 1 with a molecular weight below 600 g/mol.

8. A method of treating or preventing a disease or disorder treatable by administration of a tryptase inhibitor in a patient comprising administering to said patient in need thereof a therapeutically effective amount of one or more compounds of the formula I according to claim 1 or a pharmaceutically acceptable hydrate, solvate, salt, hydrate of a salt or solvate of a salt thereof.

9. A pharmaceutical composition comprising one or more compounds of the formula I according to claim 1 or a pharmaceutically acceptable hydrate, solvate, salt, hydrate of a salt or solvate of a salt thereof.

10. A method of treating an airway disorder in a patient comprising administering to said patient in need thereof a therapeutically effective amount of one or more compounds of the formula I according to claim 1 or a pharmaceutically acceptable hydrate, solvate, salt, hydrate of a salt or solvate of a salt thereof.

* * * * *

UNITED STATES PATENT AND TRADEMARK OFFICE
CERTIFICATE OF CORRECTION

PATENT NO.    : 6,815,557 B2
DATED         : November 9, 2004
INVENTOR(S)   : Martin It is certified that error appears in the above-identified patent and that said Letters Patent is hereby corrected as shown below:

Column 15,
Lines 21-22, please delete "-C(O)-, -C(O)-NH-"

Column 16,
Line 19, please delete "or different"
Lines 31-32, please delete "1,3-phenylene, 1,4-phenylene" and replace with
-- 1,3-phenylene, or 1,4-phenylene, --

Signed and Sealed this

Eighth Day of February, 2005

JON W. DUDAS
*Director of the United States Patent and Trademark Office*